United States Patent
Baker et al.

(10) Patent No.: US 6,290,945 B1
(45) Date of Patent: Sep. 18, 2001

(54) AQUEOUS DEODORIZER COMPOSITIONS WITH CONTROLLED RELEASE

(75) Inventors: Robert G. Baker, Ruskin, FL (US); Garland G. Corey, Milltown, NJ (US)

(73) Assignee: BBJ Environmental Solutions, Inc., Tampa, FL (US)

( * ) Notice: Subject to any disclaimer, the term of this patent is extended or adjusted under 35 U.S.C. 154(b) by 0 days.

(21) Appl. No.: 09/429,564

(22) Filed: Oct. 28, 1999

(51) Int. Cl.[7] .............................. A61L 9/00; A61L 9/015; A61L 9/04; A61K 7/32; A61K 7/035
(52) U.S. Cl. ..................... 424/76.1; 424/76.2; 424/76.4
(58) Field of Search ................ 424/65, 69, 76.1, 424/76.2, 76.4

(56) References Cited

U.S. PATENT DOCUMENTS

| | | | |
|---|---|---|---|
| 4,178,264 | * 12/1979 | Streit et al. | 252/316 |
| 4,844,721 | 7/1989 | Cox et al. | 55/85 |
| 4,844,891 | 7/1989 | Rosen et al. | 424/76.4 |
| 4,909,986 | 3/1990 | Kobayashi et al. | 424/4 |
| 5,085,849 | 2/1992 | Sampson et al. | 424/45 |
| 5,338,475 | * 8/1994 | Corey et al. | 252/102 |
| 5,895,643 | 4/1999 | Hoppe et al. | 424/65 |
| 5,942,214 | * 8/1999 | Lucas et al. | 424/65 |
| 5,955,414 | * 8/1999 | Brown et al. | 510/279 |
| 6,019,963 | * 2/2000 | Kling et al. | 424/76.1 |

* cited by examiner

Primary Examiner—Thurman K. Page
Assistant Examiner—S. Tran
(74) Attorney, Agent, or Firm—Browdy and Neimark

(57) ABSTRACT

In aqueous odor control composition comprises an evaporation control system, at least one nonionic surfactant, fragrance, and water. The odor control composition is particularly well suited for use in air ducts, crawl spaces, basements, and insulation, as the composition releases odor control ingredients at a very slow rate and does not contain any environmentally hazardous materials.

16 Claims, No Drawings

AQUEOUS DEODORIZER COMPOSITIONS WITH CONTROLLED RELEASE

FIELD OF THE INVENTION

The present invention relates to compositions for reducing odors, particularly for use on porous substrates and in air ducts.

BACKGROUND OF THE INVENTION

Air ducts, insulation, crawl spaces, attics, basements, and above ceiling spaces in offices and homes have long been a source of odors. Current products on the market to minimize odors usually contain preservatives, mild carrier solvents, and/or fragrances to attempt to mask the odors. These products are only somewhat effective.

Odor minimizing products are delivered to a substrate via the carrier solvent, and the ability of the composition to remain active in the substrate is due to a combination of the carrier solvent and surfactant. The solvents used in currently available products, however, are not sufficiently strong to allow deep penetration of the substrate. Therefore, a high concentration of the carrier solvent must be used to achieve the desired penetration. This leads to increasing levels of volatile organic compounds (VOCS) in the work place or home environment.

Certain duct odor treatment products are emulsions including a surfactant which decreases the rate of evaporation of volatile oils in the compositions. Unfortunately, neither surfactants nor surfactant combinations provide the level of stability needed in odor control compositions to inhibit evaporation of the composition while in the substrate, so that the lifespan of the product while in the substrate is severely limited. An example of such a formulation is found in Sampson et al., U.S. Pat. No. 5,085,849, which discloses an emulsified mixture of d-limonene, an ether, and water which can be used in the form of an aerosol to control odors.

Streit et al., in U.S. Pat. No. 4,178,264, disclose a gel air freshener comprising carrageenan and stearate salt, essential oils and aromatics, and a solvent component. Ethylene/polyethylene glycols and glycol mono methyl ethers are used to enhance the solubility of the stearate in processing the gel. This air freshener is not suitable for introduction into air ducts or for use on substrates, as it is a solid.

Hoppe et al.; in U.S. Pat. No. 5,895,643, describe a deodorizing composition comprising ethylene glycol monophenol ethers-2-phenoxy ethanol with Furnesol.

Rosen et al., in U.S. Pat. No. 4,844,891, disclose a preservative composition comprising mixtures of iodopropargyl compounds and a formaldehyde donor. In this case the formaldehyde donor makes it possible to use much less iodopropargyl compound than would ordinarily be necessary for preserving personal and household products.

SUMMARY OF THE INVENTION

It is an object of the present invention to overcome the aforesaid deficiencies in the prior art.

It is another object of the present invention to provide odor control compositions that can be applied to a substrate where the active ingredients are very slowly released to provide long term odor control.

It is a further object of the present invention to provide an odor control composition that can penetrate into a substrate for long term odor control.

It is another object of the present invention to provide an odor control composition having a slower evaporation rate than conventional products.

It is a further object of the present invention to provide an odor control composition having a decreased risk of harm to the health of people working or living in buildings or environments that have been treated with the odor control composition.

According to the present invention, odor control compositions are provided which include an evaporation control system, at least one nonionic surfactant, a fragrance, and water. These compositions have been found to penetrate substrates such as fiberglass insulation to a deep extent and the active ingredients are released very slowly. The compositions eliminate or reduce odors rather than merely masking them.

DETAILED DESCRIPTION OF THE INVENTION

All of the examples given herein are for purposes of illustration only, and are not for limitation. Unless otherwise noted, all percentages are by weight.

The evaporation control system preferably comprises at least one glycol ether. The evaporation control system preferably has the following characteristics:

(1) An evaporation rate in 100 ml of n-butyl acetate of between about less than 0.1 to about 0.4 (n-butyl acetate=100);

(2) Solubility in water at 20° C. between 5.0 and 100 g/100 g $H_2O$;

(3) Surface tension between 28 and 41 dynes/cm at 25° C.;

(4) Vapor pressure between 0.02 and 0.1 mm Hg at 20° C.;

(5) Ratio of-vapor pressure:evaporation rate between 0.01 and 50;

(6) Ratio of surface tension:evaporation rate greater than about 20.

Examples of evaporation control system components include dipropylene glycol n-propyl ether (DPNP), dipropylene glycol n-butyl ether(DPNB), and methyl propane diol glycol ether (MP Diol). The evaporation control system is generally present in amounts ranging from about 1–30% by weight, and preferably from about 2–10% by weight.

Methyl propane diol has an evaporation rate of less than 0.1, a solubility of 100 g/100 ml $H_2O$, a surface tension of 40.5 dynes/cm, a vapor pressure of less than 0–0.1 mmHg, a ratio of vapor pressure:evaporation rate of 1.0, and a ratio of surface tension:evaporation rate of 405. Dipropylene glycol n-butyl ether has an evaporation rate of 0.4, a solubility of 5 g/100 ml $H_2O$, a surface tension of 28.8 dynes/cm, a vapor pressure of 0.2 mmHg, a ratio of vapor pressure:evaporation rate of 0.05, and a ratio of surface tension:evaporation rate of 72.

The surfactants which can be used are nonionic surfactants which have an HLB range of about 10–16. The preferred nonionic surfactants are ethoxylated alcohols or ethoxylated alkyl phenol polyglycol ethers. Examples of such surfactants are Neutronyx 656, Stepan Chemical Co., which is nonyl phenol polyglycol ether with eleven moles of ethylene oxide, and Neodol 91.6, Shell, which is $C_9$–$C_{11}$, alcohol ethoxylated with six moles of ethylene oxide. A single nonionic surfactant can be used, as long as the HLB is between about 10 and 16. In a preferred embodiment, the composition contains two nonionic surfactants, such as the two nonionic surfactants cited above. Again, the surfactant combination must have an HLB of between about 10 and 16. The surfactants are present in the composition in amounts ranging from about 0.5 and 20% by weight, and generally between about 1 and 5% by weight. When more than one surfactant is used, the surfactants are used in amounts to produce an HLB from about 10 to 16. Other types of nonionic surfactants may be used, including $C_9$–$C_{15}$ lihear primary ethoxylates and $C_{12}$–$C_{14}$ secondary alcohol ethoxylates.

Additionally, polyoxyethylene-polyoxypropylene block copolymers, such as those marketed under the trademark PLURONIC or REVERSED PLURONIC, manufactured by BASF Wyandotte Corporation, can also be used as a surfactant.

Commercially available fragrances can be used. Selection of suitable fragrances and selection of procedures for establishing the appropriate fragrances are known to those skilled in the art. The amount of fragrance in the composition is between 0.05 and 2%, and preferably between about 0.1 and 1.0%.

Water is added to the composition to quantity sufficient to 100%.

The compositions of the present invention are manufactured by a three step process.

The composition is prepared by adding one surfactant, followed by an optional second surfactant, to distilled water, and mixing for 10 minutes. An evaporation control system is then added to the solution and mixed for 5 minutes or until clear. In a separate container, a second evaporation control system,which may be the same as the first evaporation control system, is mixed with a fragrance. The two separate solutions are then mixed together for 5 minutes or until clear. If this sequence is not followed, it is difficult to formulate the composition, as the composition is prone to separate or cloud, making the composition useless. The composition's stability is based upon following the compounding directions.

While the above methods illustrate methods for preparing the compositions of the present invention, these methods are for purposes of illustration rather than of limitation.

In use, the composition is diluted with an amount of water to make a diluted composition. The ratio of water:composition in the diluted composition ranges from 1:99 to 99:1, and is preferably from about 1:25 to about 25:1. The diluted composition is then applied to substrates such as insulation, carpet, upholstery, and textiles.

EXAMPLE

A concentrated composition was made by mixing Neodol 91.6(1.5%) and Neutronyx 658(1.5%) with distilled water for 10 minutes. DPNB(3.0%) was then added and the solution was mixed until clear(approximately 5 minutes). In a separate container, MP Diol(4.0%) was mixed with the fragrance. The MP Diol mixture was then added to the first mixture and stirred until clear(approximately 5 minutes). A diluted composition was then made using a 1:1 ratio of the concentrated composition and water. This was labeled composition A.

Odor Detection Test

An extremely odorous substance was placed on different substrates. The substrates were then treated with the below odor treating compositions.

A—composition A;
B—distilled water;
C—An antimicrobial product sold to control bacterial growth in the interior of air conditioning systems (MicroBiocide, BBJ Environmental Solutions);
D—An industrial spray ventilating system sanitizer (Envirocon);
E—An odor control spray(Odor Gun); and
F—Home spray disinfectant(Lysol).

Eight panel members were selected to provide "smell" evaluations. Each panel member was instructed to remove each container cover, sniff the head space air in the container, replace the cover, and record a judgement. The scores to be awarded were as follows:

1—no odor, 2—slight odor, 3—moderate odor, 4—fairly strong odor, 5—very strong odor Readings occurred immediately following the treatment of the substrates, and occurred once a week thereafter. Raters also ranked samples from least objectionable to most objectionable. These rankings were combined into a weighted ranking.

In the initial observation, all raters selected intensity scores of 4 or 5 for all samples. Samples A and F were rated equally as being least objectionable. Sample C was scored more objectionable. Samples B, D, and E were significantly higher and were rated as having equally objectionable scores. Over subsequent rating periods, intensity scores for samples A, C, and F fell until all three were rated 1 or 2 by the last observation (sample F received higher scores in the last evaluation than in the previous evaluation). Intensity scores for B, D, and E did not fall below 3. Sample F was the lowest during the last rating period but the score difference was not statistically significant. Samples B, D, and E continued to be awarded significantly higher ranking scores as being objectionable. Sample B rated somewhat lower than D and E in the final rating. When ranking scores were scanned, it was noted that raters,were divided with some ranking A lower, and some preferring F. Rater interviews revealed that F had a notable alcohol type odor, and A had a floral type odor. Individual preferences apparently accounted for the difference.

Safety Profile

Standard animal exposure studies were performed, using Composition A, which included: Primary Dermal Irritation Test, Eye Irritation Test, Acute Inhalation Toxicity Limit Test, and Acute Oral Toxicity Limit Test. The results were as follows:

The Primary Dermal Irritation Index(PDII) was classified as follows:

| PDII | Classification |
| --- | --- |
| Less than 2.0 | Slightly irritating |
| 2.0–5.0 | Moderately irritating |
| Greater than 5.0 | Severely irritating |

The rabbits' flesh was exposed to the composition over several days. The rabbits were measured for erythema, which is the redness of skin produced by the congestion of capillaries, and edema, which is the presence of abnormally large amounts of fluid in the intercellular tissue spaces of the body.

TABLE 1

Summary of Primary Dermal Irritation Scores

|  | Hours | | | |
| --- | --- | --- | --- | --- |
|  | 1 | 24 | 48 | 72 |
| Erythema | 0.5 | 0.0 | 0.0 | 0.0 |
| Edema | 0.0 | 0.0 | 0.0 | 0.0 |
| Total | 0.5 | 0.0 | 0.0 | 0.0 |

Primary Dermal Irritation Index:PDI for hours 1,24,48,72/4=0.1

Therefore, the diluted composition has a classification of slightly irritating.

Composition A was placed into the conjunctival sac of the right eye of each rabbit. The Maximum Mean Total Score (MMTS) was used to interpret eye irritation.

| MMTS | CLASSIFICATION |
| --- | --- |
| 0.0–0.5 | Non-irritating |
| 0.6–2.5 | Practically non-irritating |
| 2.6–15.0 | Minimally irritating |
| 15.1–25.0 | Mildly irritating |
| 25.1–50.0 | Moderately irritating |
| 50.1–80.0 | Severely irritating |
| 80.1–100.0 | Extremely irritating |
| 100.1–110.0 | Maximally irritating |

Table 2 lists the results for each rabbit.

TABLE 2

RESULTS FROM EYE IRRITATION TEST.

|  | RABBIT NO. 4813 HOURS | | | | RABBIT NO. 4814 HOURS | | | | RABBIT NO. 4815 HOURS | | | |
| --- | --- | --- | --- | --- | --- | --- | --- | --- | --- | --- | --- | --- |
|  | 1 | 24 | 48 | 72 | 1 | 24 | 48 | 72 | 1 | 24 | 48 | 72 |
| I. Cornea | | | | | | | | | | | | |
| A. Opacity | 0 | 0 | 0 | 0 | 0 | 0 | 0 | 0 | 0 | 0 | 0 | 0 |
| B. Area | 4 | 4 | 4 | 4 | 4 | 4 | 4 | 4 | 4 | 4 | 4 | 4 |
| (A × B) × 5 | 0 | 0 | 0 | 0 | 0 | 0 | 0 | 0 | 0 | 0 | 0 | 0 |
| II. Iris | | | | | | | | | | | | |
| A. Values | 0 | 0 | 0 | 0 | 0 | 0 | 0 | 0 | 0 | 0 | 0 | 0 |
| A × 5 | 0 | 0 | 0 | 0 | 0 | 0 | 0 | 0 | 0 | 0 | 0 | 0 |
| III. Conjunctivae | | | | | | | | | | | | |
| A. Redness | 1 | 1 | 0 | 0 | 1 | 1 | 0 | 0 | 1 | 1 | 0 | 0 |
| B. Chemosis | 0 | 0 | 0 | 0 | 0 | 0 | 0 | 0 | 0 | 0 | 0 | 0 |
| C. Discharge | 0 | 0 | 0 | 0 | 1 | 0 | 0 | 0 | 1 | 0 | 0 | 0 |
| (A + B + C) × 2 | 2 | 2 | 0 | 0 | 4 | 2 | 0 | 0 | 4 | 2 | 0 | 0 |
| Total | 2 | 2 | 0 | 0 | 4 | 2 | 0 | 0 | 4 | 2 | 0 | 0 |
|  | RABBIT NO. 4816 HOURS | | | | RABBIT NO. 4817 HOURS | | | | RABBIT NO. 4818 HOURS | | | |
|  | 1 | 24 | 48 | 72 | 1 | 24 | 48 | 72 | 1 | 24 | 48 | 72 |
| I. Cornea | | | | | | | | | | | | |
| A. Opacity | 0 | 0 | 0 | 0 | 0 | 0 | 0 | 0 | 0 | 0 | 0 | 0 |
| B. Area | 4 | 4 | 4 | 4 | 4 | 4 | 4 | 4 | 4 | 4 | 4 | 4 |
| (A × B) × 5 | 0 | 0 | 0 | 0 | 0 | 0 | 0 | 0 | 0 | 0 | 0 | 0 |
| II. Iris | | | | | | | | | | | | |
| A. Values | 0 | 0 | 0 | 0 | 0 | 0 | 0 | 0 | 0 | 0 | 0 | 0 |
| A × 5 | 0 | 0 | 0 | 0 | 0 | 0 | 0 | 0 | 0 | 0 | 0 | 0 |
| III. Conjunctivae | | | | | | | | | | | | |
| A. Redness | 1 | 1 | 0 | 0 | 1 | 2 | 0 | 0 | 1 | 2 | 1 | 0 |
| B. Chemosis | 0 | 1 | 0 | 0 | 0 | 0 | 0 | 0 | 0 | 1 | 1 | 0 |
| C. Discharge | 1 | 1 | 0 | 0 | 1 | 0 | 0 | 0 | 1 | 0 | 0 | 0 |
| (A + B + C) × 2 | 4 | 6 | 0 | 0 | 4 | 4 | 0 | 0 | 4 | 6 | 4 | 0 |
| Total | 4 | 6 | 0 | 0 | 4 | 4 | 0 | 0 | 4 | 6 | 4 | 0 |

The resultant MMTS for the diluted composition was 3.7.

An oral toxicity limit test was performed by administering to the animals 5,000 milligrams per kilogram of bodyweight. Results indicated that all the animals survived, gained weight, and appeared active and healthy.

An inhalation test was performed on the animals using Composition A in the atmosphere of a nominal chamber. The concentration was measured as follows:

Nominal Concentration (mg/L)=Composition A Mixture Used(mg)/Average Air Flow(LPM)×Total Time(min)

The nominal concentration was measured to be 202.18 mg/L. Results showed that all the animals survived exposure to the composition mixture atmosphere and gained weight over the 14-day period.

Evaporation Test

An evaporation test was performed using various dilutions of the concentrated composition. An amount was weighed into an evaporation dish and allowed to set at room temperature for a period of several days. An initial total weight(grams) was taken of the product and dish. Subsequent weights were taken at specific times. Weight loss for a time period were calculated as % wt. loss. The results are shown below in Table 3.

TABLE 3

| Dilution (H₂O/Composition) | Day 1 | Day 2 | Day 6 |
| --- | --- | --- | --- |
| 95/5 | 39 | 79 | 88 |
| 90/10 | 38 | 78 | 87 |
| 75/25 | 37 | 77 | 86 |
| 50/50 | 38 | 77 | 87 |
| 0/100 | 38 | 78 | 82 |

The above results concluded that a uniform weight loss consistency is observed over many dilutions.

The odor control compositions of the present invention are effective in freshening and deodorizing the interiors of both lined and unlined ductwork, and can also be used to freshen and deodorize basements, crawl spaces, attics, and areas above suspended ceilings where objectionable odors originate. The compositions have the dual impact of neutralizing foul odors arising from particulate or vapors, and the source of these aerosols in substrates to which they are applied.

The compositions are particularly effective on deep fiberglass substrates, such as those found in insulation and air duct liners, where the compositions must penetrate deeply to react with the contaminants that are the source of the foul odors. The compositions have excellent wetting ability, so that they are highly effective on textiles and other porous surfaces such as carpets and upholstery.

The compositions are effective with an extremely low concentration of active chemical ingredients. The compositions can be applied without the requirement for evacuating the premises during application or use of special clothing or equipment. The compositions can readily be applied with a compressed air sprayer or fogging device. There is no need to rinse surfaces after application. The composition will not bleach, stain, or discolor most fabrics and surfaces.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

What is claimed is:

1. An aqueous odor control composition in the form of a clear liquid consisting essentially of:

from about 1 to about 30% by weight of an evaporation control system comprising at least one glycol ether; from about 0.5 to about 20% by weight of at least one nonionic surfactant, from about 0.5 to about 2% by weight of fragrance, and the remainder water.

2. The composition according to claim 1 consisting essentially of from about 2–20% of evaporation control system, from about 0.8 to about 3.75% of a first nonionic surfactant, from about 0.8 to about 3.75% by weight of a second nonionic surfactant, from about 0.1 to about 1.25% by weight of a fragrance, and water to 100%.

3. The composition according to claim 1 wherein the at least one glycol ether is selected from the group consisting of dipropylene glycol n-propyl ether, dipropylene glycol n-butyl ether, and methyl propane diol glycol either.

4. The composition according to claim 2 wherein the at least one glycol ether is selected from the group consisting of dipropylene glycol n-propyl ether, dipropylene glycol n-butyl ether, and methyl propane diol glycol either.

5. A method for making the composition according to claim 1, comprising adding at least one nonionic surfactant to water to form a first solution, mixing an evaporation control system with fragrance in a separate container to form a second solution, and then mixing the first and the second solutions together.

6. The composition according to claim 1 wherein the at least one surfactant is selected from the group consisting of ethoxylated alcohols; ethoxylated alkyl phenol polyglycol ethers; $C_{9-15}$ linear primary ethoxylates; $C_{12-14}$ secondary alcohol ethoxylates; polyoxyethylene-polyoxypropylene block copolymers; and mixtures thereof.

7. The composition according to claim 6 wherein the surfactant is an ethoxylated alcohol phenol polyglycol ether.

8. The composition according to claim 6 wherein the surfactant is an ethoxylated alcohol.

9. The composition according to claim 8 wherein the ethoxylated alcohol is a $C_{9-11}$ alcohol ethoxylated with six moles of ethylene oxide.

10. The composition according to claim 6 wherein the at least one surfactant is a mixture of an ethoxylated alkyl phenol polyglycol ether and an ethoxylated alcohol.

11. The composition according to claim 10 wherein the ethoxylated alkyl phenol polyglycol either is nonyl phenol polyglycol ether ethoxylated with eleven moles of ethylene oxide and the ethoxylated alcohol is a $C_{9-11}$ alcohol ethoxylated with six moles of ethylene oxide.

12. The composition according to claim 1 wherein the evaporation control system has the following characteristics:

(a) an evaporation rate in 100 ml of butyl acetate of about less than about 0.1 to about 0.4;

(b) solubility in water at 20° C. between about 5.0 and about 100 g/100 g water;

(c) surface tension between about 28 and about 41 dynes/cm at 25° C.;

(d) vapor pressure between about 0.02 and about 0.1 mm Hg at 20° C.;

(e) ratio of vapor pressure:evaporation rate between about 0.01 and about 50;

(f) ratio of surface tension:evaporation rate greater than about 20.

13. The composition according to claim 12 wherein the evaporation control system comprises a mixture of dipropylene glycol n-propyl ether, dipropylene glycol n-butyl ether, and, optionally, methyl propane diol.

14. The composition according to claim 1 wherein the evaporation control system comprises a mixture of dipropylene glycol n-propyl ether, dipropylene glycol n-butyl ether, and methyl propane diol.

15. A method for controlling odors in locations selected from the group consisting of porous substrates, air ducts, insulation, crawl spaces, attics, basements, and above ceiling spaces, comprising applying to said location an effective amount of a composition according to claim 1.

16. The method according to claim 15 wherein said porous substrate is fiberglass.

* * * * *